(12) United States Patent
Dittmann

(10) Patent No.: US 7,856,978 B2
(45) Date of Patent: Dec. 28, 2010

(54) PROCESS FOR OPERATING AN ANESTHESIA APPARATUS

(75) Inventor: Ralf Dittmann, Lübeck-Blankensee (DE)

(73) Assignee: Dräger Medical GmbH, Lübeck (DE)

( * ) Notice: Subject to any disclaimer, the term of this patent is extended or adjusted under 35 U.S.C. 154(b) by 918 days.

(21) Appl. No.: 11/183,125

(22) Filed: Jul. 14, 2005

(65) Prior Publication Data

US 2006/0090757 A1    May 4, 2006

(30) Foreign Application Priority Data

Oct. 28, 2004    (DE)    ........................ 10 2004 052 398

(51) Int. Cl.
| | |
|---|---|
| A61M 15/00 | (2006.01) |
| A61M 16/10 | (2006.01) |
| A61M 16/00 | (2006.01) |
| H05B 3/00 | (2006.01) |
| A62B 7/00 | (2006.01) |
| A62B 7/10 | (2006.01) |

(52) U.S. Cl. ........................... 128/203.12; 128/202.26; 128/203.13; 128/203.14; 128/203.15; 128/203.27; 128/205.11; 128/205.28

(58) Field of Classification Search ............ 128/202.26, 128/203.12–203.15, 203.27, 205.11, 205.28, 128/910

See application file for complete search history.

(56) References Cited

U.S. PATENT DOCUMENTS

| | | | | |
|---|---|---|---|---|
| 5,067,492 | A | * | 11/1991 | Yelderman et al. .......... 600/532 |
| 5,509,406 | A | * | 4/1996 | Kock et al. ............. 128/203.14 |
| 5,537,992 | A | * | 7/1996 | Bjoernstijerna et al. 128/203.14 |
| 5,875,783 | A | * | 3/1999 | Kullik ................... 128/204.18 |
| 5,931,161 | A | * | 8/1999 | Keilbach et al. ....... 128/204.22 |
| 6,095,137 | A | * | 8/2000 | Wallroth et al. ........ 128/203.26 |
| 6,289,891 | B1 | * | 9/2001 | Cewers .................. 128/203.12 |
| 6,422,237 | B1 | * | 7/2002 | Engel et al. ............ 128/204.21 |
| 6,634,355 | B2 | * | 10/2003 | Colas .................... 128/203.12 |
| 2002/0014236 | A1 | * | 2/2002 | Dittmann et al. ....... 128/203.25 |

FOREIGN PATENT DOCUMENTS

| | | |
|---|---|---|
| DE | 199 58 532 C1 | 1/2001 |
| GB | 2040715 A | 9/1980 |

* cited by examiner

*Primary Examiner*—Patricia M Bianco
*Assistant Examiner*—Nihir Patel
(74) *Attorney, Agent, or Firm*—McGlew & Tuttle, P.C.

(57) ABSTRACT

An anesthesia apparatus with a breathing circuit (1) has improved initiation of anesthesia for the patient. The gas mixture dispensed into the breathing circuit (1) is circulated in a first operating state without release to a patient until a preset anesthetic concentration is set in the breathing circuit (1). The respiration of the patient connected to the anesthesia apparatus takes place in a subsequent second operating state with the gas mixture set in the first operating state.

20 Claims, 1 Drawing Sheet

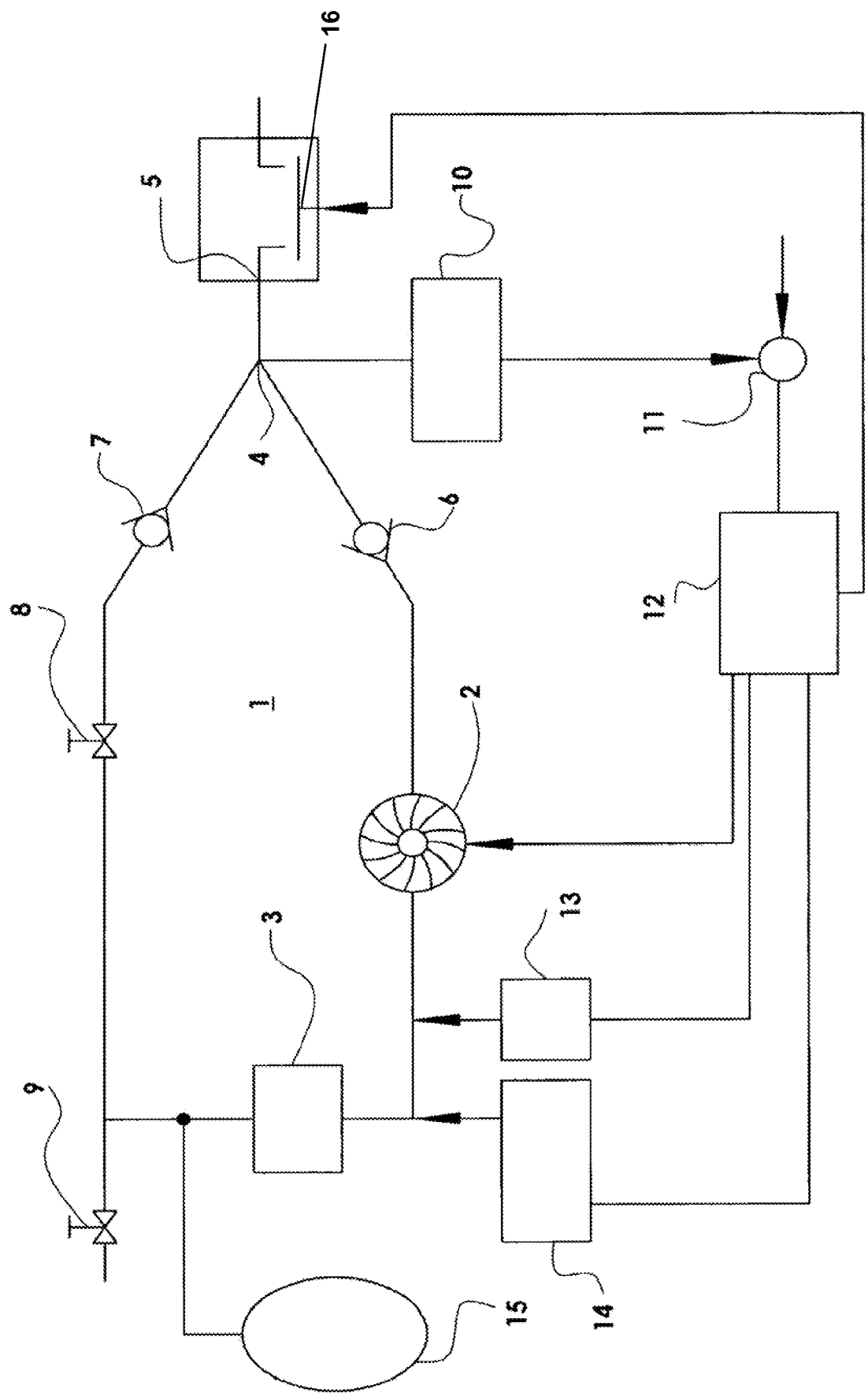

PROCESS FOR OPERATING AN ANESTHESIA APPARATUS

CROSS REFERENCE TO RELATED APPLICATION

This application claims the benefit of priority under 35 U.S.C. §119 of German Application DE 10 2004 052 398.3 of Oct. 28, 2004, the entire contents of which application is hereby incorporated by reference in its entirety.

FIELD OF THE INVENTION

The present invention pertains to a process for operating an anesthesia apparatus with a breathing circuit.

BACKGROUND OF THE INVENTION

A process for operating an anesthesia apparatus or respirator with a breathing circuit is disclosed in DE 199 58 532 C1, where the speed of the gas delivery element is changed to set the respiration.

Inhalation anesthesia can be initiated for a patient so far only in a time-consuming manner and with incomplete monitoring. It is necessary to operate with a high fresh gas flow for a relatively long time in case of a half-closed rebreathing system. This is in order to exchange the gases in the breathing system corresponding to the desired concentration and as a function of the volume of the breathing circuit and the patient's parameters.

Even though a desired rapid initiation of anesthesia is guaranteed in case of direct feed of the fresh gas, which fresh gas contains $O_2$ and $N_2O$, enriched with a volatile anesthetic, with a half-open system with a separate fresh gas outlet, it is disadvantageous that the monitoring of the pressure and the gas concentration is not ensured. A technical safety system is difficult to embody. Moreover, the patient must be disconnected and connected to the circulation system after the initiation of the anesthesia.

SUMMARY OF THE INVENTION

The object of the present invention is to provide a process for operating an anesthesia apparatus with improved initiation of anesthesia in terms of speed, wherein disconnection after the initiation of the anesthesia is to be avoided, but monitoring of the patient shall continue to be ensured.

According to the invention, a process is provided for operating an anesthesia apparatus with a breathing circuit. The gas mixture is dispensed into the breathing circuit, circulating in a first operating state, without release to a patient until a preset anesthetic concentration is established in the breathing circuit. The respiration of the patient connected to the anesthesia apparatus takes place in a subsequent second operating state with the gas mixture set in the first operating state.

A switchover may be performed from the first into the second operating state when a preset anesthetic concentration is reached in the breathing circuit. The switchover from the first into the second operating state is advantageously performed when a preset anesthetic concentration is reached in the breathing circuit and the patient connection is opened.

The anesthetic concentration set in the first operating state in the breathing circuit may be detected by means of an infrared optical measurement. A closing means in the patient connection may be actuated by means of a control means, so that the closing means is closed in the first operating state and opened in the second operating state.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

BRIEF DESCRIPTION OF THE DRAWINGS

In the drawings:

The only FIGURE schematically shows an anesthesia rebreathing circuit for carrying out the process according to the invention;

DESCRIPTION OF THE PREFERRED EMBODIMENTS

The breathing circuit 1 has an adjustable gas delivery means 2, which is preferably designed here as a radial flow compressor. The radial flow compressor can be set highly dynamically, allowing exceptional real time control in respect to the speed and the rate of delivery. The $CO_2$ absorber 3 is a component consisting of soda lime or another material, which can absorb $CO_2$ from the breathing circuit 1. The two one-way valves (first and second check valves) 6, 7 define by their installation the inspiration branch and the expiration branch to and from the Y-piece 4 with the patient connection 5.

The adjustable shut-off valves 8, 9 are used to set the pressure in the breathing circuit and in the line leading away from the breathing circuit. A reversible breathing gas reservoir 15, designed especially as a breathing gas bag, is provided for manually supporting the respiration in case of need. The gas-measuring means 10 detects the anesthetic concentration in the breathing circuit 1 for the patient monitoring preferably by means of an infrared optical measurement. After comparison 11 with a preset value for the anesthetic concentration by means of the control means 12, the current measured value is used to set the gas dispensing device 14 for a mixture of the gases oxygen, air and/or $N_2O$ (laughing gas) as well as to set the anesthetic dispensing device 13 for a volatile anesthetic. The breathing circuit 1 is connected at the Y-piece 4 or at the patient connection 5 in the first operating state, so that release of the gas mixture from the breathing circuit 1 to a patient is not possible. The target concentration is preset and the control means 12 controls the feed of the gases and of the volatile anesthetic or anesthetics until the target concentration is reached, so that the anesthesia apparatus with the breathing circuit 1 is prepared for initiating the anesthesia for the patient. In the second operating state of the anesthesia apparatus, the patient is connected with the breathing circuit 1 via the Y-piece 4 and the patient connection 5, and he immediately receives the desired gas concentrations. The state of the patient connection 5 is controlled by control means 12 acting on a closing means (actuatable closing device) 16 as shown in the FIGURE. Since the breathing circuit 1 is completely at the preset gas concentration level, the optimal gas mixture is always supplied and readjusted for the patient. The patient monitoring is continuously ensured because the patient does not need to be disconnected and the sensor system is always ready for measurement and available for the breathing circuit 1.

While a specific embodiment of the invention has been shown and described in detail to illustrate the application of the principles of the invention, it will be understood that the invention may be embodied otherwise without departing from such principles.

What is claimed is:

1. A process for operating an anesthesia apparatus, the process comprising:
provprovviding a breathing circuit with a first one-way valve and a second one-way valve;
providing a patient connection with an actuatable closing device;
providing a gas dispensing means for dispensing a gas mixture;
providing an anesthetic dispensing means for dispensing anesthetic into said gas mixture;
dispensing said gas mixture into the breathing circuit;
providing a control means connected to said actuatable closing device, said gas dispensing means and said anesthetic dispensing means for controlling a flow of anesthetic from said anesthetic dispensing means to said gas mixture and for controlling said actuatable closing device such that said control means controls feed of said gas mixture to a patient via said actuatable closing device;
circulating the gas mixture in the breathing circuit in a first operating state, said control means controlling said flow of anesthetic from said anesthetic means into said gas mixture such that a preset anesthetic concentration is established in said gas mixture in said first operating state, said control means controlling feed of said gas mixture to the patient such that said gas mixture is not released to the patient when said gas mixture is in said first operating state, said control means controlling said actuatable closing device such that said actuatable closing device is in a closed position in said first operating state, whereby said breathing circuit is not in communication with the patient in said first operating state; and
respirating the patient connected to the anesthesia apparatus in a subsequent second operating state such that said gas mixture with said preset anesthetic concentration is received by the patient in said second operating state, said control means controlling said actuatable closing device such that said actuable closing device is open in said second operating state, wherein said gas mixture with said preset anesthetic concentration passes through said actuatable closing device in said second operating state.

2. A process in accordance with claim 1, further comprising the steps of:
providing a gas measuring means for measuring an anesthetic concentration of said gas mixture, said gas measuring means being connected to said control means and said breathing circuit, said control means controlling said flow of anesthetic into said gas mixture based on said measured anesthetic concentration, wherein switchover is performed from the first into the second operating state when said preset anesthetic concentration is reached in the breathing circuit.

3. A process in accordance with claim 2, wherein switchover from the first into the second operating state is performed when said preset anesthetic concentration is reached in the breathing circuit and a patient connection is opened.

4. A process in accordance with claim 1, wherein the anesthetic concentration set in the first operating state in the breathing circuit is detected by means of an infrared optical measurement.

5. A process in accordance with claim 1, wherein said breathing circuit defines a first flow path in said first operating state, said gas mixture being circulated in said first flow path in said first operating state, said breathing circuit, said actuatable closing device and said patient connection defining a second flow path in said second operating state, wherein the patient receives said gas mixture with said preset anesthetic concentration via said second flow path in said second operating state.

6. A process for operating an anesthesia apparatus, the process comprising the steps of:
providing a breathing circuit with a first check valve and a second check valve;
connecting a patient connection to the breathing circuit, said patient connection comprising an actuatable closing device;
connecting an anesthetic dispensing device to the breathing circuit;
connecting a gas dispensing device to the breathing circuit;
dispensing a breathing gas into the breathing circuit via said gas dispensing device;
circulating said dispensed breathing gas within the breathing circuit in a first operating state;
connecting a gas measuring device to said breathing circuit;
measuring an anesthetic concentration of said dispensed breathing gas;
connecting a control device to said gas measuring device;
controlling said actuatable closing device with said control device such that said closing device is in a closed position in said first operating state;
comparing said measured anesthetic concentration of said dispensed breathing gas to a preset anesthetic concentration with said control device;
controlling a flow of anesthetic gas to said dispensed breathing gas from said anesthetic dispensing device with said control device when said dispensed breathing gas is in said first operating state such that said dispensed breathing gas within said breathing circuit has said preset anesthetic concentration to form a gas mixture;
controlling flow of said dispensing breathing gas to the patient such that said dispensed breathing gas in said first operating state is not released to the patient;
controlling said actuatable closing device with said control device such that said closing device is in an open position in a second operating state after forming said gas mixture in said first operating state; and
connecting a patient to the anesthesia apparatus in said second operating state and initiating respiration with the gas mixture set in the first operating state, said closing device being in said open position in said second operating state, whereby the patient receives said gas mixture having said preset anesthetic concentration via said one of said check valves and said actuatable closing device.

7. A process in accordance with claim 6, wherein the breathing circuit provided includes an inhalation line, an inhalation valve connected to said inhalation line, an exhalation line, an exhalation valve connected to said exhalation line, a gas delivery device connected to said inhalation line and a $CO_2$ absorber connected to said gas delivery device.

8. A process in accordance with claim 7, wherein the gas dispensing device is a radial flow compressor setting a speed and the rate of delivery of the gas mixture for respiration.

9. A process in accordance with claim 6, wherein anesthesia concentration in the breathing circuit is measured with a gas-measuring means during said first operating state and said dispensing of the anesthetic gas is controlled during said first operating state based on a detected gas concentration.

10. A process in accordance with claim 9, wherein the gas-measuring means is an infrared optical measurement device.

11. A process in accordance with claim 6, further comprising:
  measuring anesthetic concentration of said gas mixture delivered to the patient with a gas-measuring means during said second operating state; and
  dispensing anesthetic gas during said second operating state based on said measured anesthetic concentration such that said gas mixture maintains said preset anesthetic concentration.

12. A process in accordance with claim 6, wherein when the preset anesthetic concentration is reached, the breathing circuit is switched over from the first operating state into the second operating state.

13. A process in accordance with claim 6, wherein when the preset anesthetic concentration is reached in the breathing circuit and said patient connection is opened the breathing circuit is switched over from the first operating state into the second operating state.

14. A process in accordance with claim 6, wherein said breathing circuit defines a first flow path in said first operating state, said dispensed breathing gas being circulated in said first flow path in said first operating state, said breathing circuit, said actuatable closing device and said patient connection defining a second flow path in said second operating state, wherein the patient receives said gas mixture with said preset anesthetic concentration via said second flow path in said second operating state.

15. An anesthesia apparatus, comprising:
  a breathing circuit comprising an inspiration check valve and an expiration check valve;
  a patient connection connected to the breathing circuit, said patient connection including an actuatable closing device;
  an anesthetic dispensing device connected to the breathing circuit;
  a gas dispensing device connected to the breathing circuit;
  a gas delivery device, said gas delivery device being arranged in said breathing circuit;
  a control device connected to said gas delivery means, said actuatable closing device, said anesthetic dispensing device and said gas dispensing device for controlling a dispensing of a breathing gas mixture into the breathing circuit and for controlling a dispensing of an anesthetic gas into the breathing circuit and actuating said actuatable closing device such that said actuatable closing device is closed to establish a first operating state and opened to establish a second operating state, said control device controlling said gas delivery device such that said gas delivery device circulates a gas mixture including the dispensed gas in the first operating state without release to a patient until a preset anesthetic concentration is established in the gas mixture within the breathing circuit and initiating respiration in the second operating state with the gas mixture set in the first operating state, said gas mixture with said preset anesthetic concentration being delivered to the patient via said actuatable closing device and said inspiration check valve in said second operating state.

16. An apparatus in accordance with claim 15, further comprising a gas-measuring device measuring anesthetic concentration in the breathing circuit, said gas-measuring device being connected to said control device, said control device controlling the dispensing of anesthetic gas during said first operating state and said second operating state based on the measured gas concentration.

17. An apparatus in accordance with claim 16, wherein the breathing circuit provided includes an inhalation line, an inhalation valve connected to said inhalation line, an exhalation line, an exhalation valve connected to said exhalation line, and a $CO_2$ absorber connected to said gas delivery device, said gas delivery device being connected to said inhalation line.

18. An apparatus in accordance with claim 17, wherein said gas delivery device is a radial flow compressor setting a speed and the rate of delivery of the gas mixture for respiration.

19. An apparatus in accordance with claim 16, wherein said gas-measuring device measuring anesthetic concentration in the breathing circuit is an infrared optical measurement device.

20. An apparatus in accordance with claim 15, wherein when a preset anesthetic concentration is reached in the breathing circuit, the control device opens the patient connection to the breathing circuit to switch over from the first operating state into the second operating state, said breathing circuit defining a first flow path in said first operating state, said gas mixture being circulated in said first flow path in said first operating state, said breathing circuit, said actuatable closing device and said patient connection defining a second flow path in said second operating state, wherein the patient receives said gas mixture with said preset anesthetic concentration via said second flow path in said second operating state.

* * * * *